United States Patent [19]

Boden

[11] Patent Number: 4,720,481
[45] Date of Patent: Jan. 19, 1988

[54] CYCLOHEXENYL PYRIDINE DERIVATIVES, ORGANOLEPTIC USES OF SAME AND PROCESSES FOR PREPARING SAME

[75] Inventor: Richard M. Boden, Ocean, N.J.

[73] Assignee: International Flavors & Fragrances Inc., New York, N.Y.

[21] Appl. No.: 53,349

[22] Filed: May 22, 1987

[51] Int. Cl.$^4$ ............................................. A61K 7/46
[52] U.S. Cl. ........................................ 512/10; 252/8.6; 252/174.11
[58] Field of Search .................... 512/10; 546/350; 252/8.6, 174.11

[56] References Cited

U.S. PATENT DOCUMENTS 3,716,543  2/1973  Hall et al. .......................... 546/344
4,374,051  2/1983  Neef et al. ............................ 512/10
4,539,143  9/1985  Boden et al. ...................... 252/522 R

OTHER PUBLICATIONS

Doering et al, J.A.C.S., vol. 75, pp. 4738–4740 (1953).
Chem. Abstracts, 1956, No. 2577h (abstract of article by Petrov, et al, J. Gen. Chem., USSR, 25, 703–7 (1955).

Primary Examiner—James H. Reamer
Attorney, Agent, or Firm—Arthur L. Liberman

[57] ABSTRACT

Described are cyclohexenyl pyridine derivatives defined according to the structures:

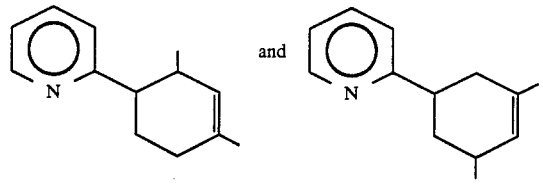

formed in admixture when vinyl pyridine having the structure:

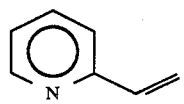

is reacted with 2-methyl-1,3-pentadiene having the structure:

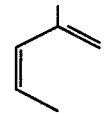

as well as organoleptic uses thereof in augmenting or enhancing the aroma of perfume compositions, perfumed articles and perfumed polymers.

12 Claims, 7 Drawing Figures

FIG.1

GLC PROFILE FOR EXAMPLE I.
CRUDE

FIG.2

GLC PROFILE FOR EXAMPLE I.

FIG.3

CAPILLARY GLC PROFILE FOR BULKED
FRACTIONS 5-10 OF EXAMPLE I.

FIG.4

GLC PROFILE FOR EXAMPLE I.

FIG. 5

NMR SPECTRUM FOR FRACTION 6 OF EXAMPLE I.

CYCLOHEXENYL PYRIDINE DERIVATIVES, ORGANOLEPTIC USES OF SAME AND PROCESSES FOR PREPARING SAME

BACKGROUND OF THE INVENTION

There is a continuing search for materials having desirable fragance properties. Such materials are sought either to replace costly natural materials or to provide new fragrances, perfume types or fragrance nuances which have not, heretofore, been available.

Especially desirable qualities for substance having interesting fragrances are stability in a wide variety of perfumed articles and perfume compositions, ease of manufacture, intensity and pleasantness of aroma.

Particularly desirable in the perfume, cologne and perfumed article area are fragrance nuances which can be described as rosey, fruity and green with galbanum undertones.

Cycloalkenyl pyridine derivatives have been previously described in the perfume area, for example, in U.S. Pat. No. 3,716,543 issued on Feb. 13, 1973 wherein the compound having the structure:

is disclosed at column 4, line 37 and the genus defined according to the structure:

is described at column 2, broadly; wherein at column 2, lines 45-50 G is indicated to represent a chain of alkyl substituted or unsubstituted carbon atoms completing a cycloalkenyl ring including but not limited to monocyclic and bicyclic moieties; wherein m is an integer of 1,2,3 or 4; wherein the $R_1$ group is either hydrogen or alkyl; and wherein $R_8$, $R_9$ and $R_{10}$ each represents hydrogen or lower alkyl. U.S. Pat. No. 3,716,543 describes the use of the above genus (broadly) and the above compound in perfumery.

The compounds having the structures:

are indicated to have been prepared by Petrov, et al, J. Gen. Chem. USSR 25, 703-7 (1955) but the organoleptic properties of these compounds are not set forth therein.

Nothing in the prior art discloses the specific mixture of the compounds having the structures:

prepared according to the process of my invention having the organoleptic uses as set forth herein.

BRIEF DESCRIPTION OF THE DRAWINGS

(Conditions: 6'×0.24" 10% SE-30 column programmed at 220 isothermal).

(Conditions: 6'×0.25" 10% SE-30 column programmed at 220° C. isothermal).

(Conditions: Capillary SE-30 column programmed at 80°–220° C. at 4° C. per minute).

DETAILED DESCRIPTION OF THE DRAWINGS

Figure 1:
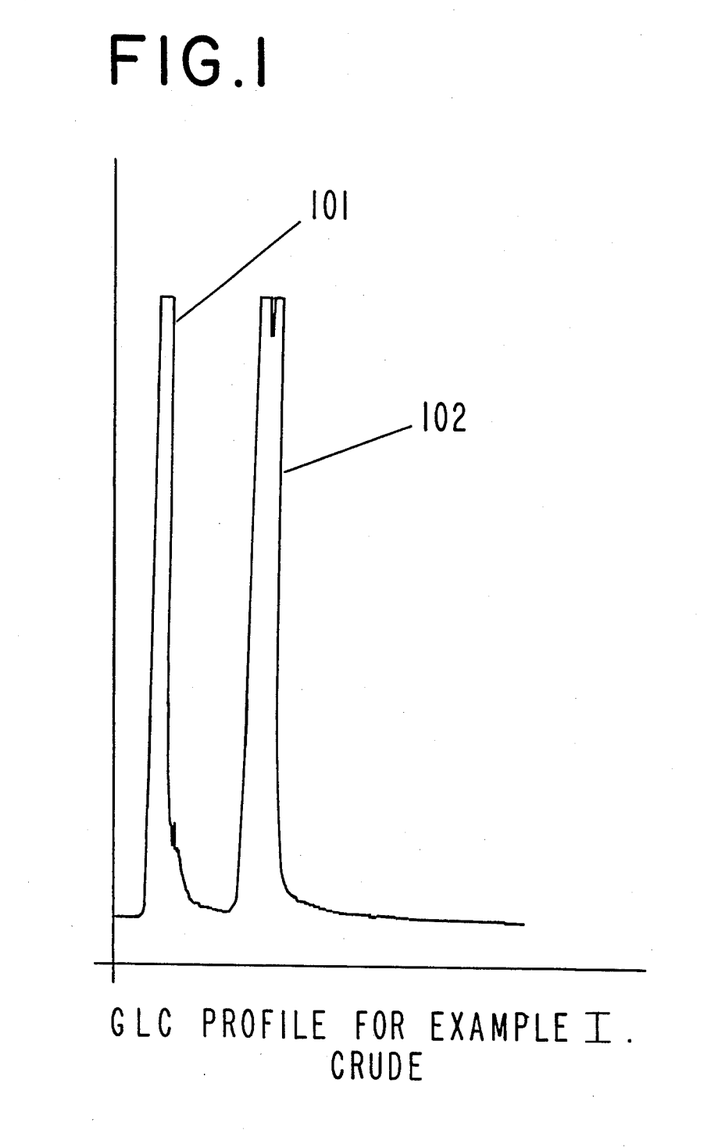
FIG. 1 is the GLC profile for the crude reaction product of Example I containing the compounds having the structures.
Figure 2:
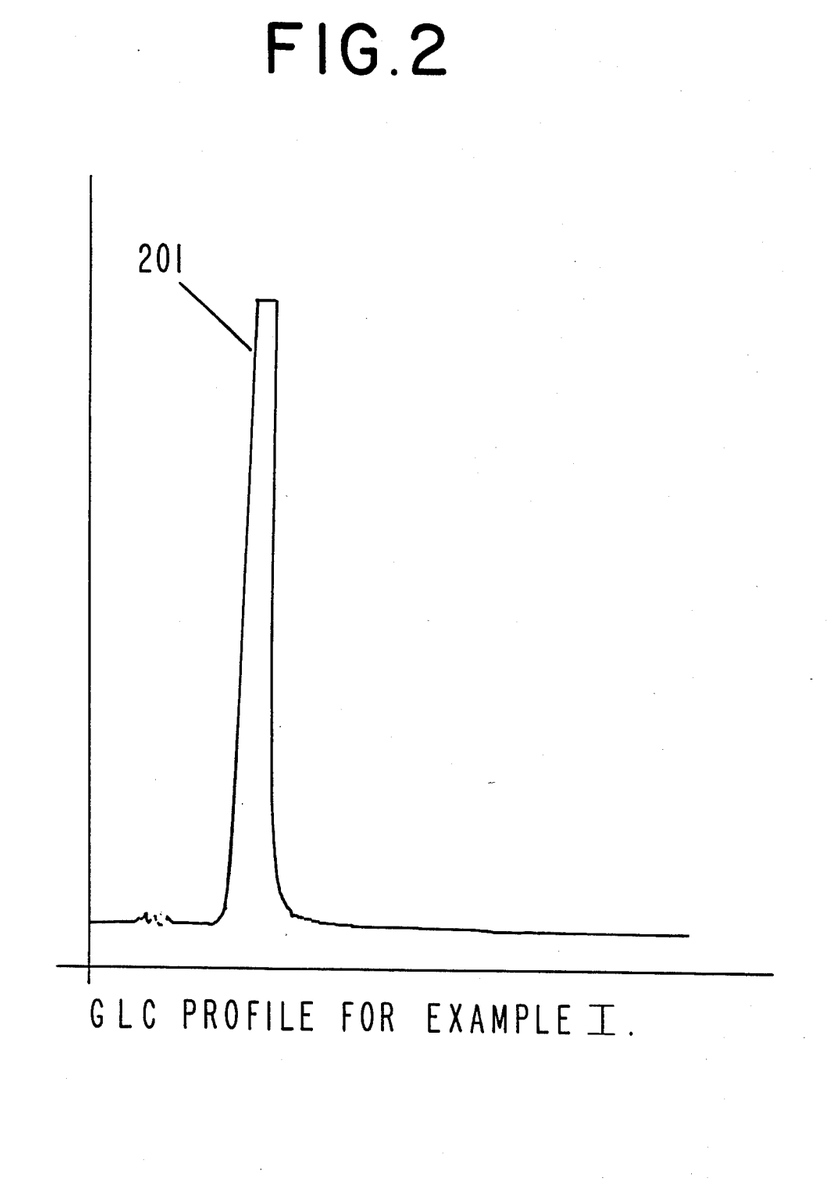
FIG. 2 is the GLC profile for bulked fractions 2 and 3 of the first distillation of the reaction product of Example I containing the compounds having the structures.

FIG. 1 is the GLC profile for the crude reaction product of Example I containing the compounds having the structures:

The peak indicated by reference numeral 101 is the peak for the unreacted starting products which is a mixture of vinyl pyridine having the structure:

and 2-methyl-1,3-pentadiene having the structure:

The peak indicated by reference numeral 102 is the peak for the mixture of compounds having the structures:

FIG. 2 is the GLC profile for bulked fractions 2 and 3 of the first distillation of the reaction product of Example I containing the mixture of compounds having the structures:

The peak indicated by reference numeral 201 is the peak for the mixture of compounds having the structures:

(Conditions: 6′×0.25″ 10% SE-30 column programmed at 220° C. isothermal).

Figure 4:
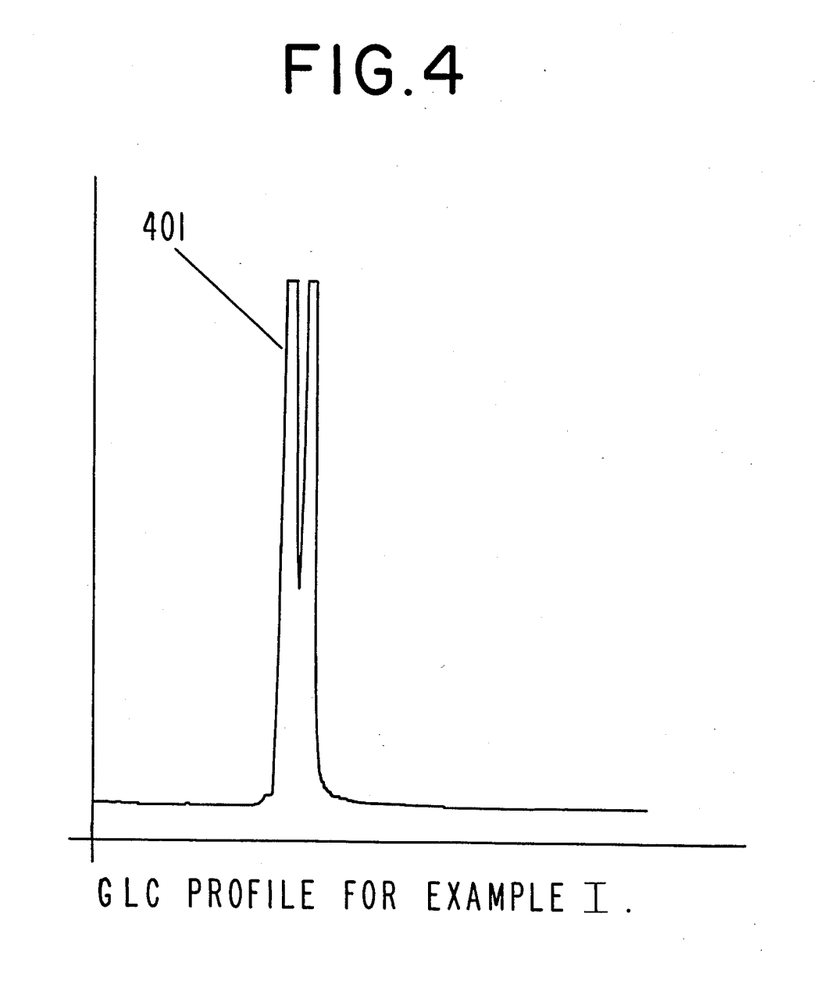
FIG. 4 is the GLC profile for the final bulking of the distillation products of the reaction product of Example I containing the compounds having the structures.

FIG. 4 is the GLC profile for the final bulking of the distillation product of the reaction product of Example I containing the mixture of compounds having the structures:

The peak indicated by reference numeral 401 is the peak for the two compounds having the structures:

(Conditions: 6'×0.25" 10% Se-30 column programmed at 220° C. isothermal).

Figures 6, 7:
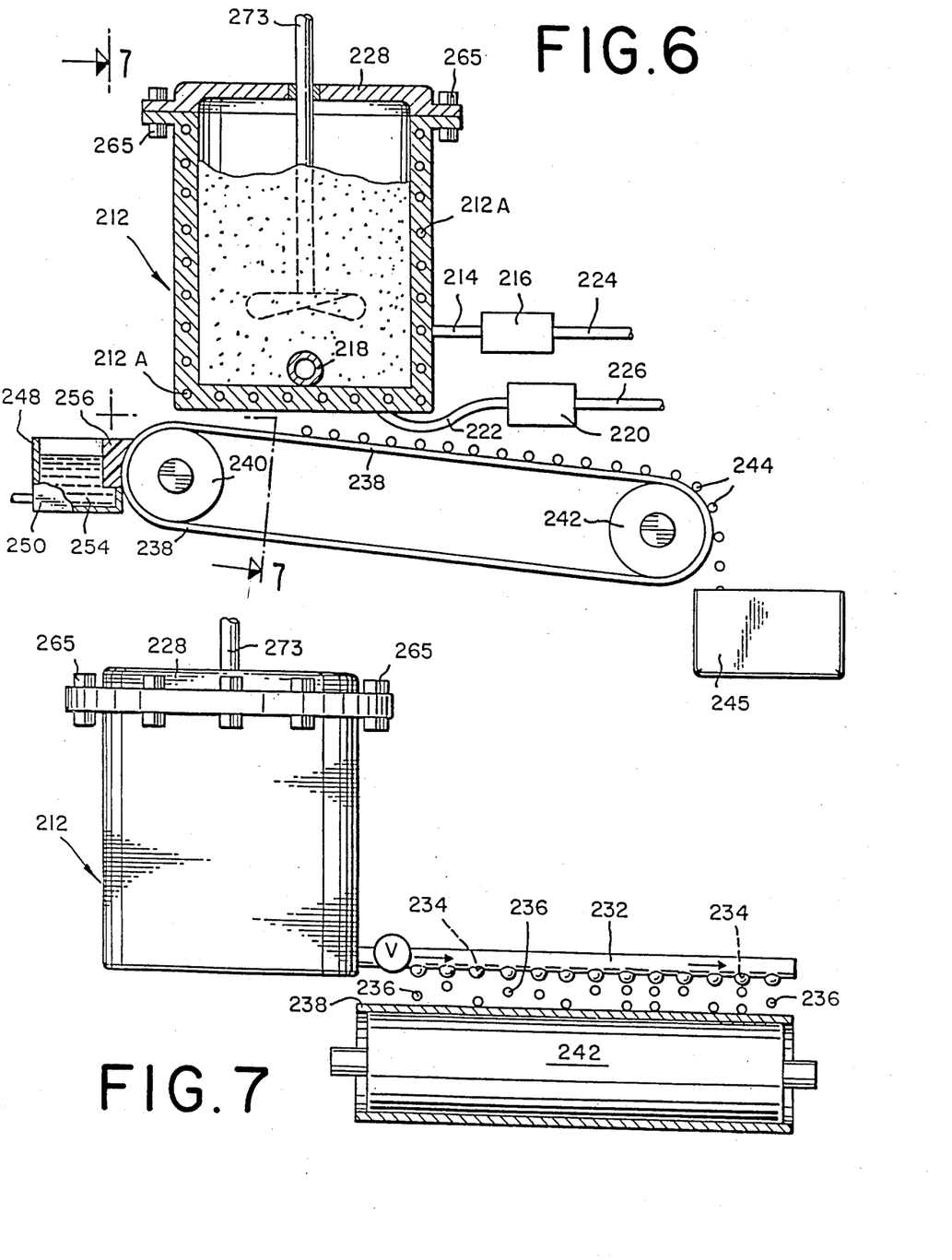
FIG. 6 is a partial side elevation and partial sectional view of an apparatus for forming polymer pellets scented with the cyclohexenyl pyridine derivatives of my invention.
FIG. 7 is a section taken on line 7—7 of FIG. 6.

Referring to FIGS. 6 and 7 in particular, the apparatus used in producing polymeric fragrances containing the cyclohexenyl pyridine derivatives of my invention comprises a device for forming scented polyolefin (for example) pellets which comprises a vat or container 2101 into which a mixture of polyolefin such as polyethylene and an aromatic substance or scented material is placed (in this case the cyclohexenyl pyridine derivatives of my invention). The container is closed by an airtight lid 228 and clamped to the container by bolts 265. A stirrer 273 traverses the lid or cover 228 in airtight manner and is rotated in a suitable manner. A surrounding cylinder 212 having heating coils which are supplied with electric current through cable 224 from a rheostat or control 216 is operated to maintain a temperature inside the container 2101 such that polyethylene or other thermoplastic polymer in the container will be maintained in the molten or liquid state. It has been found advantageous to employ a colorles odorless polymer (e.g., polyethylene) with a viscosity ranging between 180 and 220 saybolt seconds and having a melting point in the range of 200°–280° F. The heater 2201 is operated to maintain the upper portion of the container 2101 within a temperature range from 250°–350° F. The bottom portion of the container 218 is heated by means of heating coils 222 heated through a control 220 connected thereto through a connecting wire 226 to maintain a lower portion of the container 218 within a temperature range of from 250°–350° F.

Thus, polymer (e.g., polyethylene) is added to container 2101 and is heated from 10–12 hours whereafter a scented aroma imparing material (the cyclohexenyl pyridine derivatives of my invention) is added quickly to the melt. The material must be compatible with polyolefin and forms a homogeneous liquid melt therewith. The scented material is of a type of the particular aroma desired and formulated specifically for the scenting purpose for which the polyolefin will be employed.

Generally, about 5–30% by weight of the scented material (the cyclohexenyl pyridine derivatives of my invention) is added to the polyolefin.

After the scent imparting material (e.g., the cyclohexenyl pyridine derivatives of my invention) is added to container 2101, the mixture is stirred for a few minutes, for example, 5–15 minutes and maintained within the temperature range as indicated previously by heating coils 212 and 218, respectively. The controls 216 and 220 are connected through cables 224 and 226 to a suitable power supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer (e.g., polyolefin) and aroma mixture will continuously drop through orifices 234 downwardly from the conduit 232. During this time, the temperature of the polymer (e.g., polyolefin) and aroma mixture in the container 2101 (e.g., the cyclohexenyl pyridine derivatives of my invention) is accurately controlled so that a temperature in the range of from about 210°–275° F. will exist in the conduit 232. The regulation of the temperature through the control 216 and the control 2201 is essential in order to insure temperature balance to provide for the continuous dropping or dripping of molten polymer (e.g., polyethylene) and scenting material (e.g., the cyclohexenyl pyridine derivatives of my invention) mixture through the orifices 234 at a rate which will insure the formation of droplets 236 which will fall downwardly onto a moving conveyor belt 238 trained to run between conveyor wheels 240 and 242 beneath the conduit 232.

When the droplets 236 fall onto the conveyor 238 they form pellets 244 which harden almost instantaneously and fall off the end of the conveyor 238 into a container 259 which is advantageously filled with water or some other suitable cooling liquid to insure the rapid cooling of each of the pellets. The pellets 244 are then collected from the container 259 and utilized in processes as illustrated, infra.

A feature of this aspect of the process of my invention is the provision for moistening the conveyor belts 238 to insure rapid formation of the solid polymer (e.g., polyolefin) scented pellets 244 without sticking to the belt. The belt 238 is advantageously of a material which will not normally stick to a melted plastic but a moistening means 248 insures a sufficiently cold temperature of the belt surface for adequate formation of the pellets 244. The moistening means comprises a container 259 which is continuously fed with water 252 to maintain a level 254 for moistening a sponge element 256 which bears against the exterior surface of the belt 238.

THE INVENTION

The invention comprises the novel product as well as novel processes according to which such products are manufactured, this specific embodiments of which are described hereinafter by way of example and in accordance with which it is now preferred to practice the invention.

Briefly, the present invention provides the cyclohexenyl pyridine derivatives defined according to the structures:

useful in augmenting or enhancing the aroma of consumable materials including perfume compositions, colognes and perfumed articles.

The cyclohexenyl pyridine derivatives of my invention augment or enhance the aroma of perfume compositions, colognes and perfumed articles by augmenting or enhancing the rosey, fruity and green aromas and galbanum undertones.

Thus, the cyclohexenyl pyridine derivatives of my invention are described as having rosey, fruity and green aroma nuances with galbanum undertones.

The cyclohexenyl pyridine derivatives of my invention are prepared by reacting 2-vinyl pyridine having the structure:

with 2-methyl-1,3-pentadiene having the structure:

according to the reaction:

at a temperature in the range of from about 140° C. up to about 200° C. and at a pressure in the range of from about 50 psig up to about 500 psig; preferably at a temperature in the range of from about 170° C. up to about 190° C. and a pressure of from about 80 psig up to about 120 psig.

At the end of the reaction the reaction mass is fractionally distilled in order to provide products having properties causing them to be suitable for augmenting or enhancing the aroma of perfume compositions, perfumed articles and colognes.

The cyclohexenyl pyridine derivatives of my invention and one or more auxiliary perfume ingredients, including, for example, alcohols, aldehydes, ketones, terpinic hydrocarbons, nitriles, esters, amines other than the cyclohexenyl pyridine derivatives of my invention, natural synthetic oils and synthetic essential oils may be admixed so that the combined odors of the individual components produce a pleasant and desired fragrance, particularly and preferably in the floral, rose, herbaceous and galbanum fragrances.

Such perfume compositions usually contain (a) the main note or the "bouquet" or foundation stone of the composition; (b) modifiers which round off and accompany the main note; (c) fixatives which include odorous compositions which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics, however, the over-all sensory effect of the perfume composition will be at least the sum total of the effects of each of the ingredients. Thus, the cyclohexenyl pyridine derivatives of my invention can be used to alter, modify or enhance the aroma characteristics of a perfume composition, for example, by utilizing or moderating the olfactory reaction contributed by another ingredient in the composition.

The amount of the cyclohexenyl pyridine derivatives of my invention which will be effective in perfume compositions as well as in perfumed articles and colognes depends on many factors, including the other ingredients, their amounts and the effects which are desired. It has been found that perfume compositions containing as little as 0.01% of the cyclohexenyl pyridine derivatives of my invention or even less (e.g., 0.005%) can be used to impart, augment or enhance rosey, fruity and green aroma nuances with galbanum undertones to soaps, cosmetics or other products. The amount employed can range up to 70% of the fragrance components and will depend on consideration of cost, nature of the end product, the effect desired on the finished product and the particular fragrance sought.

The cyclohexenyl pyridine derivatives of my invention are useful (taken alone or together with other ingredients in perfume coompositions) as (an) olfactory component(s) in detergents and soaps, space odorants and deodorants, perfumes, colognes, toilet water, bath preparations, such as creams, deodorants, hand lotions and sun screens, powders, such as talcs, dusting powders, face powders and the like. When used an (an) olfactory component(s) in perfumed articles as little as 0.1% of the cyclohexenyl pyridine derivatives of my invention or composition containing a high proportion of the cyclohexenyl pyridine derivatives of my invention will suffice to impart, augment or enhance intense long-lasting rosey, fruity and green aroma nuances and galbanum undertones.

The range of the cyclohexenyl pyridine derivatives of my invention useful in perfumed articles including solid or liquid anionic, cationic, nonionic and zwitterionic detergents, soaps, space odorants and deodorants, bath preparations, such as creams, deodorants, hand lotions and sun screens; powders, such as talcs, dusting powders, face powders and the like and perfumed polymers may vary from as little as 0.1% to as much as 5% of the cyclohexenyl pyridine derivatives of my invention.

In addition, the perfume composition or fragrance composition of my invention can contain a vehicle or carrier for the cyclohexenyl pyridine derivatives or composition containing the cyclohexenyl pyridine derivatives of my invention. The vehicle can be a liquid, such as an alcohol, such as ethyl alcohol, a non-toxic glycol, such as propylene glycol or the like. The carrier can also be an absorbent solid, such as gum (i.e., gum arabic, guar gum, xanthan gum or the like) or components for encapsulating the composition (such as gelatin when encapsulation is carried out by means of coacervation or such as a urea formaldehyde prepolymer when encapsulation is carried out by forming a polymeric wall around a liquid perfume scenter.

The following Example I serves to illustrate a method for preparation of the cyclohexenyl pyridine derivatives of my invention.

The examples following Example I (Examples II, et seq.) show methods for utilizing the organoleptic properties of the cyclohexenyl pyridine derivatives of my invention. It will be understood that these examples are illustrative and the invention is to be considered as restricted thereto only as indicated in the appended claims.

EXAMPLE I

PREPARATION OF MIXTURE OF 2(2,4-DIMETHYL-3-CYCLOHEXENYL) PYRIDINE AND 2(3,5-DIMETHYL-3-CYCLOHEXENYL) PYRIDINE

Reaction:

Into a 2 liter autoclave equipped with heater is placed 500 grams (4.76 moles) of 2-vinyl pyridine and 585 grams (3.1 moles) of 2-methyl-1,3-pentadiene. The autoclave is sealed and heated to a temperature of 175° C. and maintained at that temperature for two hours (pressure equal 120 psig). At the end of the one hour period, the autoclave is opened and cooled and the product is distilled, first on a "rushover" column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 53/91 | 94/108 | 3/2.6 | 57 |
| 2 | 94 | 118 | 0.8 | 120 |
| 3 | 90 | 165 | 0.8 | 133 |

Fractions 2 and 3 are bulked for redistillation and redistilled on a 2' Goodloe column yielding the following fractions:

| Fraction No. | Vapor Temp. (°C.) | Liquid Temp. (°C.) | Vacuum mm/Hg. Pressure | Reflux Ratio | Weight of Fraction |
|---|---|---|---|---|---|
| 1 | 63/63 | 103/104 | 0.5 | 4:1 | 12 |
| 2 | 65 | 106 | 0.5 | 4:1 | 21 |
| 3 | 67 | 107 | 0.4 | 4:1 | 22 |
| 4 | 67 | 107 | 0.4 | 4:1 | 20 |
| 5 | 67 | 108 | 0.4 | 4:1 | 22 |
| 6 | 67 | 110 | 0.4 | 4:1 | 23 |
| 7 | 69 | 112 | 0.4 | 4:1 | 24 |
| 8 | 72 | 115 | 0.4 | 4:1 | 22 |
| 9 | 72 | 115 | 0.4 | 4:1 | 27 |
| 10 | 72 | 122 | 0.4 | 4:1 | 21 |
| 11 | 72 | 160 | 0.4 | 4:1 | 18 |
| 12 | 68 | 220 | 0.4 | 4:1 | 16 |

Fractions 5–10 are bulked and Fractions 5–10 consist essentially of the compounds having the structures:

Fractions 5–10 have a pleasant and long-lasting rosey, fruity and green aroma with galbanum undertones.

FIG. 1 is the GLC profile for the crude reaction product. The peak indicated by reference numeral 102 is the peak for the compounds having the structures:

The peak indicated by reference numeral 101 is the peak for unreacted starting materials, 2-vinyl pyridine and 2-methyl-1,3-pentadiene.

Figure 3:
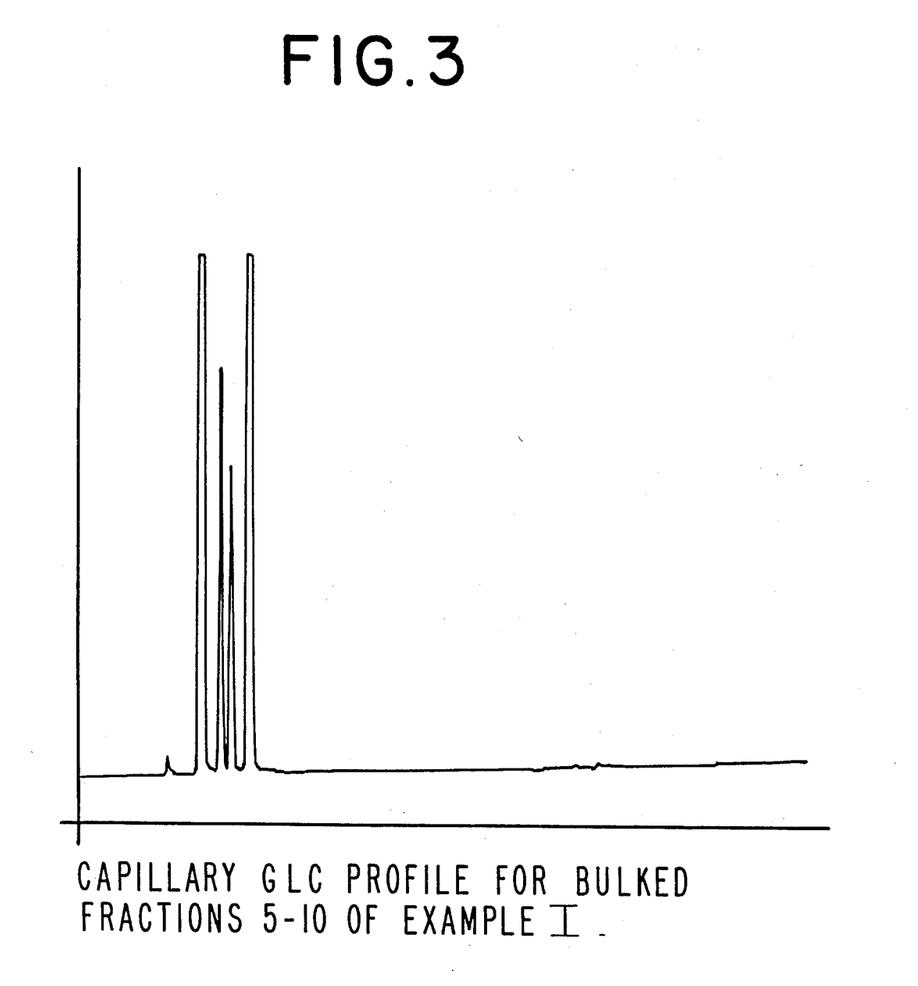
FIG. 3 is the GLC profile for bulked fractions 5-10 of the second distillation of the reaction product of Example I containing the compounds having the structures.

FIG. 2 is the GLC profile for the bulked Fractions 2 and 3 of the first distillation. The peak indicated by reference numeral 201 is the peak for the mixture of compounds having the structures:

FIG. 3 is a capillary GLC profile for bulked Fractions 5–10 of the above distillation (Conditions: Capillary SE-30 column programmed at 80°–220° C. at 4° C. per minute).

FIG. 4 is the GLC profile for the final bulking of the foregoing distillation product. The peak indicated by reference numeral 401 is the peak for the mixture of compounds having the structures:

and

Figure 5:
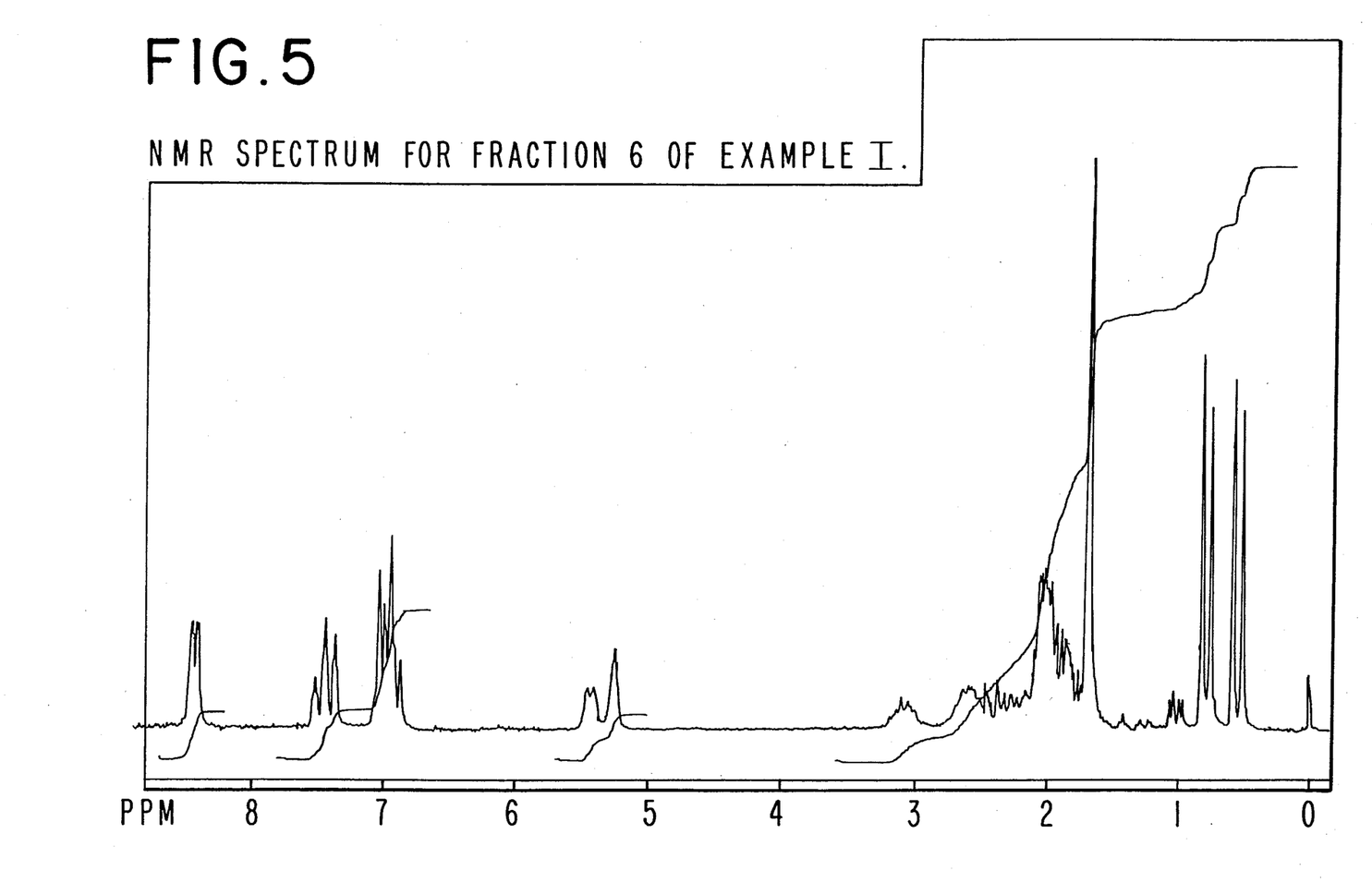
FIG. 5 is the NMR spectrum for fraction 6 of the distillation of the reaction product of Example I containing the compounds having the structures.

FIG. 5 is the NMR spectrum for the above reaction product (Fraction 6 of the second distillation) containing the compounds having the structures:

and in admixture.

EXAMPLE II

The following "rose" composition is prepared:

| Ingredients | Parts by Weight |
|---|---|
| Linalyl acetate | 135.0 |
| Bergamont oil | 275.0 |
| Citronellol | 135.0 |
| Lavandulol | 135.0 |
| Portugal oil | 135.0 |
| Neroli oil | 40.5 |
| Jasmine oil | 20.5 |
| Jasmine absolute | 20.5 |
| Neroliol, Bigarade | 28.0 |
| Rosemary oil | 28.0 |
| Mixture of compounds having the structures: | 23.5 |

[structures]

and

[structure]

prepared according to Example I.

| Rose absolute | 13.5 |
| Hydroxy citronellol | 13.5 |
| Cyclopentadecanolide 10% in diethyl phthalate | 7.0 |

The addition of the mixture of compounds defined according to the structures:

and produced according to Example I in the quantity given adds an excellent long-lasting distinctive fruity and green topnotes with galbanum undertones. Accordingly, the perfume composition can be described as "rosey with fruity and green topnotes and galbanum undertones".

EXAMPLE III

PREPARATION OF A COSMETIC POWDER COMPOSITION

A cosmetic powder is prepared by mixing in a ball mill, 100 grams of talcum powder with 0.25 grams of one of each of the perfumery substances set forth in Table I below. Each of the cosmetic powders has an excellent intense aroma as set forth in Table I below:

TABLE I

| Perfume Substance | Perfumery Evaluation |
|---|---|
| Mixture of compounds having the structures: [structures] and [structure] prepared according to Example I (bulked Fractions 5-10). | A rosey, fruity and green aroma profile with galbanum undertones. |
| Perfume composition of Example II. | Rosey with fruity and green topnotes and galbanum undertones. |

EXAMPLE IV

PERFUMED LIQUID DETERGENT

Concentrated liquid detergents with aromas as set forth in Table I of Example III (which detergents are prepared from Lysine salt of n-dodecyl benzene sulfonic acid as more specifically described in U.S. Pat. No. 3,948,818 issued on Apr. 6, 1976, the specification for which is incorporated by reference herein), are prepared containing each of the substances set forth in Table I of Example III, supra. They are prepared by adding and homogeneously mixing the appropriate quantity of perfumery substance as set forth in Table I of Example III in the liquid detergent. The detergents all possess aromas as set forth in Table I of Example III, the intensity increasing with greater concentrations of perfumery substance of Table I of Example III, supra.

EXAMPLE V

PREPARATION OF A COLOGNE AND HANDERCHIEF PERFUME

The perfume substances of Table I of Example III, supra, are incorporated into colognes at concentrations of 1.5%, 2.0%, 2.5%, 3.0% and 4.0% in 80%, 85% and 90% aqueous ethanols; and into handkerchief perfume compositions at concentrations of 10%, 15%, 20%, 25% and 30% (in 85%, 90% and 95% aqueous ethanols). Distinct and definitive aromas as set forth in Table I of Example III are imparted to the cologne and to the handkerchief perfume compositions.

EXAMPLE VI

PREPARATION OF A DETERGENT COMPOSITION

A total of a 100 grams of a detergent powder (a nonionic detergent powder containing a proteo lytic enzyme prepared according to Example I of Canadian Letters Patent No. 985,190 issued on Mar. 9, 1976, the disclosure of which is incorporated by reference herein), is mixed with 0.15 grams of each of the substances set forth in Table I of Example III, supra, until substantially homogeneous compositions are obtained. These compositions have excellent aromas as set forth in Table I of Example III.

EXAMPLE VII

PREPARATION OF SOAP

Each of the perfumery substances of Table I of Example III are incorporated into soap (LVU-1) at 0.1% by weight of each substance. After two weeks in the oven at 90° F. each of the soaps showed no visual effect from the heat. Each of the soaps manifested an excellent aroma as set forth in Table I of Example III, supra.

EXAMPLE VIII

PREPARATION OF SOAP COMPOSITION

One hundred grams of soap chips (IVORY ®, registered trademark of the Procter & Gamble Co. of Cincinnati, Ohio) are mixed individually with one gram each of the perfumery substances of Table I of Example III, supra, until a homogeneous composition is obtained. The homogeneous composition is then treated under three atmospheres pressure at 180° C. for a period of three hours and the resulting liquid is placed into a soap mold. The resulting soap cakes, on cooling, manifest excellent aromas as set forth in Table I of Example III, supra.

EXAMPLE IX

PREPARATION OF A SOLID DETERGENT COMPOSITION

A detergent is prepared from the following ingredients according to Example I of Canadian Letters Patent No. 1,007,948 (the specification for which is incorporated by reference herein):

| Ingredients | Parts by Weight |
| --- | --- |
| "Neodol 45-II" (a $C_{14}$–$C_{15}$ alcohol ethoxylated with 11 moles of ethylene oxide) | 12 |
| Sodium carbonate | 55 |
| Sodium citrate | 20 |
| Sodium sulfate, water | q.s. |
| brighteners | |

This detergent is a "phosphate-free" detergent. A total of 100 grams of this detergent is admixed separately with 0.15 grams of each of the perfume substances of Table I of Example III, supra. The detergent samples each have excellent aromas as set forth in Table I of Example III, supra.

EXAMPLE X

Utilizing the procedure of Example I at column 15 for U.S. Pat. No. 3,632,396, the specification for which is incorporated by reference herein, a non-woven cloth substrate useful as a dryer-added fabric softening article of manufacture is prepared wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.);
   57 percent $C_{20\text{-}22}$ HAPS
   22 percent isopropyl alcohol
   20 percent antistatic agent
   1 percent of one of the perfume substances of Table I of Example III, supra.

A fabric softening composition prepared as set forth above having the above aroma characteristics as set forth in Table I of Example III, supra, essentially consists of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of substrate. The aroma set forth in Table I of Example III is imparted in a pleasant manner to the headspace in the dryer on operation thereof, using said dryer-added fabric softening non-woven fabric.

What is claimed is:

1. A mixture of compounds having the structures:

2. A mixture consisting essentially of the compounds having the structures:

produced by the process comprising the steps of reacting 2-vinyl-pyridine having the structure:

with 2-methyl-1,3-pentadiene having the structure:

at a temperature in the range of from about 140° C. up to about 200° C. and a pressure in the range of from about 50 psig up to about 500 psig.

3. A process for augmenting or enhancing the aroma of a perfume composition, cologne or perfumed article comprising the step of intimately admixing with said perfume composition, cologne or perfumed article, an aroma augmenting or enhancing quantity of the product defined according to claim 1.

4. A process for augmenting or enhancing the aroma of a perfume composition, cologne or perfumed article comprising the step of intimately admixing with said perfume composition, cologne or perfumed article, an aroma augmenting or enhancing quantity of the product defined according to claim 2.

5. The process of claim 3 wherein the cyclohexenyl pyridine is added to a perfume composition.

6. The process of claim 3 wherein the cyclohexenyl pyridine is added to a perfumed article and the perfumed article is a solid or liquid anionic, cationic, nonionic or zwitterionic detergent.

7. The process of claim 3 wherein the cyclohexenyl pyridine is added to a perfumed article and the perfumed article is a fabric softener composition or dryer-added fabric softener article.

8. The process of claim 3 wherein the cyclohexenyl pyridine is added to a perfumed polymer.

9. The process of claim 4 wherein the cyclohexenyl pyridine composition is added to a perfumed article and the perfumed article is a solid or liquid anionic, cationic, nonionic or zwitterionic detergent.

10. The process of claim 4 wherein the cyclohexenyl pyridine is added to a perfume composition or cologne.

11. The process of claim 4 wherein the cyclohexenyl pyridine is added to a perfumed article and the perfumed article is a perfumed polymer.

12. The process of claim 4 wherein the cyclohexenyl pyridine is added to a perfumed article and the perfumed article is a fabric softener composition or dryer-added fabric softener article.

* * * * *